United States Patent [19]

Murayama et al.

[11] Patent Number: 5,756,863
[45] Date of Patent: May 26, 1998

[54] PROCESS FOR PREPARING OPTICALLY ACTIVE CYCLOHEXANOL DERIVATIVES

[75] Inventors: Toshiyuki Murayama; Takaji Matsumoto; Takashi Miura, all of Kanagawa, Japan

[73] Assignee: Takasago International Corporation, Tokyo, Japan

[21] Appl. No.: 730,021

[22] Filed: Oct. 11, 1996

[30] Foreign Application Priority Data

Oct. 12, 1995 [JP] Japan ................................. 7-289151

[51] Int. Cl.$^6$ ................................................. C07C 29/145
[52] U.S. Cl. .................................................... 568/814
[58] Field of Search ................................. 568/814, 813

[56] References Cited

U.S. PATENT DOCUMENTS

| | | | |
|---|---|---|---|
| 3,968,147 | 7/1976 | Solodar | 568/814 |
| 4,440,936 | 4/1984 | Riley | 568/814 |
| 5,066,815 | 11/1991 | Sayo et al. | 568/812 |
| 5,210,332 | 5/1993 | Taketomi et al. | 568/813 |
| 5,227,538 | 7/1993 | Buchwald et al. | 568/814 |
| 5,596,113 | 1/1997 | Douglas et al. | 556/14 |

*Primary Examiner*—James H. Reamer
*Attorney, Agent, or Firm*—Sughrue, Mion, Zinn, Macpeak & Seas, PLLC

[57] ABSTRACT

A process for producing an optically active cyclohexanol derivative represented by formula (I):

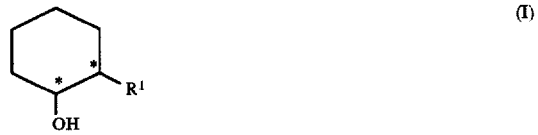

wherein $R^1$ represents an alkyl group having 1 to 4 carbon atoms, a hydroxyl group, or a protected hydroxyl group, comprising asymmetrically hydrogenating a cyclohexanone derivative in the presence of a catalyst system composed of a transition metal compound (e.g., transition metal complex), a base (e.g., KOH), and a nitrogen compound (e.g., an amine compound).

7 Claims, No Drawings

PROCESS FOR PREPARING OPTICALLY ACTIVE CYCLOHEXANOL DERIVATIVES

FIELD OF THE INVENTION

This invention relates to a process for preparing optically active cyclohexanol derivatives, more particularly to a practical process for preparing optically active cyclohexanol derivatives useful in various applications, for examples, as intermediate for pharmaceuticals or optically active ligands.

BACKGROUND OF THE INVENTION

Known methods for asymmetric synthesis of optically active alcohols include (1) an enzymatic method using bread yeast, etc. and (2) asymmetric hydrogenation of a carbonyl compound using a metal complex catalyst. In particular, many proposals have been made to date for the asymmetric hydrogenation route as follows.

1) Asymmetric hydrogenation of a carbonyl compound having a functional group using an optically active ruthenium catalyst (R. Noyori (ed.), *Asymmetric Catalysis in Organic Synthesis*, pp. 56–82 (1994)).
2) Hydrogen shift type reduction using a ruthenium, rhodium or iridium asymmetric complex catalyst (*Chem. Rev.*, Vol. 92, pp. 1051–1069 (1992)).
3) Asymmetric hydrogenation using a tartaric acid-modified nickel catalyst (*Yukagaku*, pp. 828–831 (1980) and Y. Izumi (ed.), *Advances in Catalysis*, Vol. 32, p. 215 (1983)).
4) Asymmetric hydrosilylation (J. D. Morrison (ed.), *Asymmetric Synthesis*, Vol. 5, Chap. 4 (1985) and *J. Organomet. Chem.*, Vol. 346, pp. 413–424 (1988)).
5) Borane reduction in the presence of an asymmetric ligand (*J. Chem. Soc., Perkin Trans. 1*, pp. 2039–2044 (1985) and *J. Am. Chem. Soc.*, Vol. 109, pp. 5551–5553 (1987)).
6) Asymmetric hydrogenation of an aromatic ketone using potassium hydroxide, an optically active diamine, and a ruthenium asymmetric complex catalyst (*J. Am. Chem. Soc.*, Vol. 117, pp. 2675–2676 (1995)).
7) Diastereoselective asymmetric hydrogenation of a racemic carbonyl compound, e.g., asymmetric hydrogenation of a β-ketoester compound using a ruthenium asymmetric complex catalyst (*J. Am. Chem. Soc.*, Vol. 111, pp. 9134–9135 (1989), ibid, Vol. 115, pp. 144–152 (1993), and *J. Chem. Soc., Chem. Commun.*, pp. 609–610 (1991)).

Of the above-described methods, the process of using an enzyme produces alcohols of relatively high optical purity but is limited in kind of applicable substrates. Besides, the absolute configuration of the resulting alcohols is limited. The processes using a transition metal catalyst for asymmetric hydrogenation produce optically active alcohols at high selectivity from substrates having a functional group in the molecule thereof, such as a keto-acid, but are unsatisfactory in terms of reaction rate and ineffective on simple carbonyl compounds having no functional group in the molecule thereof, and require a very expensive optically active amine compound. The diastereoselective asymmetric hydrogenation of a racemic carbonyl compound is effective only on those substrates which are accompanied with racemization through enolization, such as β-ketoester compounds.

SUMMARY OF THE INVENTION

An object of the present invention is to provide a highly active catalyst system capable of diastereoselectively producing an optically active alcohol from a racemic carbonyl compound and a novel process for synthesizing an optically active alcohol using the catalyst system.

The present invention relates to a process for producing an optically active cyclohexanol derivative represented by formula (I):

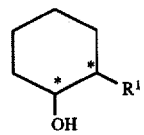

wherein $R^1$ represents an alkyl group having 1 to 4 carbon atoms, a hydroxyl group, or a protected hydroxyl group, comprising reacting a cyclohexanone derivative represented by formula (II):

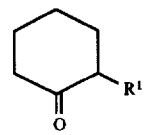

wherein $R^1$ is as defined above, with hydrogen in the presence of a catalyst system for asymmetric hydrogenation which is composed of a transition metal compound, a base, and a nitrogen compound.

In a preferred embodiment of the above process, the transition metal compound is a complex of a transition metal of the group VIII of the Periodic Table, the base is selected from an alkali metal compound, an alkaline earth metal compound, and a quaternary ammonium salt, and the nitrogen compound is an amine compound.

In a still preferred embodiment of the above process, the transition metal compound is a compound represented by formula (III):

$$M^1X_mL_n \quad (III)$$

wherein $M^1$ represents a transition metal of the group VIII of the Periodic Table, e.g., Ru, Rh, Ir or Pt; X represents a hydrogen atom, a halogen atom, a carboxyl group, a hydroxyl group, or an alkoxy group; L represents an optically active phosphine ligand; and m and n each represent an integer, and/or the base is selected from a metallic compound represented by formula (IV):

$$M^2Y \quad (IV)$$

wherein $M^2$ represents a metal selected from an alkali metal and an alkaline earth metal; and Y represents a group selected from a hydroxyl group, an alkoxy group, a mercapto group, or a naphthyl group, or a quaternary ammonium salt.

DETAILED DESCRIPTION OF THE INVENTION

The starting compound for use in the invention is a 2-substituted cyclohexanone compound represented by formula (II).

In formula (II), $R^1$ represents an alkyl group having 1 to 4 carbon atoms, a hydroxyl group, or a protected hydroxyl group. Specific examples of $R^1$ are alkyl groups, e.g., methyl, ethyl, propyl, isopropyl, butyl, isobutyl, sec-butyl, and tert-butyl groups; a hydroxyl group; and protected hydroxyl groups, e.g., methoxy, ethoxy, propoxy, isopropoxy, butoxy, benzyloxy, acetoxy, trimethylsilyloxy, triethylsilyloxy, tert-butyldimethylsilyloxy, dimethylphenylsilyloxy, and diphenylmethylsilyloxy groups.

The transition metal compound which constitutes the asymmetric hydrogenation catalyst system according to the invention is preferably a transition metal complex represented by formula (III).

In formula (III), $M^1$ is a transition metal of the group VIII, such as ruthenium, rhodium, iridium or platinum, with ruthenium being preferred. X is a hydrogen atom, a halogen atom, a carboxyl group, a hydroxyl group or an alkoxy group. L is an optically active phosphine ligand.

Examples of the optically active phosphine ligand as L include 2,2'-bis(diphenylphosphino)-1,1'-binaphthyl (hereinafter abbreviated as BINAP), 2,2'-bis(di-p-tolylphosphino)-1,1'-binaphthyl (Tol-BINAP), 2,2'-bis(di-p-chlorophenylphosphino)-1,1'-binaphthyl (p-Cl-BINAP), 2,2'-bis(di-p-methoxyphenylphosphino)-1,1'-binaphthyl (p-OMe-BINAP), 2,2'-bis(di-p-tert-butylphenylphosphino)-1,1'-binaphthyl (p-tert-Bu-BINAP), 2,2'-bis(di-3,5-dimethylphenylphosphino)-1,1'-binaphthyl (DM-BINAP), 2,2'-bis(diphenylphosphino)-1,1'-octahydrobinaphthyl ($H_8$-BINAP), 2,2'-bis(di-3,5-dimethylphenylphosphino)-1,1'-octahydrobinaphthyl ($H_8$-DM-BINAP), 2,2'-bis(diphenylphosphino)-6,6'-dimethyl-1,1'-biphenyl (BIPHEMP), and 2,2'-bis(dicyclohexylphosphino)-6,6'-dimethyl-1,1'-biphenyl (BICHEP), 1-[1,2-bis(diphenylphosphino)ferrocenyl]ethylenediamine (BPPFA), 2,3-bis(diphenylphosphino)butane (CHIRAPHOS), 1-cyclohexyl-1,2-bis(diphenylphosphino)ethane (CYCPHOS), a 1-substituted-3,4-bis(diphenylphosphino) pyrrolidine (DEGPHOS), 2,3-o-isopropylidene-2,3-dihydroxy-1,4-bis(diphenylphosphino)butane (DIOP), 1,2-bis[(o-methoxyphenyl)phenylphosphino)ethane (DIPAMP), a 1,2-bis(2,5-disubstituted phosphorano)benzene (DUPHOS) (see J. Am. Chem. Soc., Vol. 115, pp. 10125-10138 (1993)), 5,6-bis(diphenylphosphino)-2-norbornene (NORPHOS), N,N'-bis(diphenylphosphino)-N,N'-bis[(R)-1-phenylethyl]ethylenediamine (PNNP), 1,2-bis(diphenylphosphino)propane (PROPHOS), and 2,4-bis(diphenylphosphino)pentane (SKEWPHOS).

Monodentate optically active phosphine ligands represented by formula $PR^2R^3R^4$, wherein $R^2$, $R^3$ and $R^4$ are all different groups or at least one of them is an optically active group, can also be used. Examples of such monodentate phosphine ligands are isopropylmethylphenylphosphine, cyclohexyl(o-anisyl)methylphosphine, diphenylmenthylphosphine, 1-[2-(diphenylphosphino) ferrocenyl]ethyl methyl ether, and 2-(diphenylphosphino)-2'-methoxy-1,1'-binaphthyl.

n for bidentate phosphine ligands is 1 to 2 and that for monodentate phosphine ligands is 3 to 4. Optically active phosphine ligands which can be used in the invention are not limited to the foregoing examples. Neither is the transition metal element limited to ruthenium.

The group VIII transition metal complex is used usually at a molar ratio of 1/100 to 1/100,000, preferably 1/500 to 1/20,000, to the reaction substrate, 2-substituted cyclohexanone, while varying depending on the type of the reaction vessel, the type of the reaction, or economy.

In formula (IV) representing the base which can be used in the catalyst system of the invention, $M^2$ is an alkali metal or an alkaline earth metal, and Y is a hydroxyl group, an alkoxy group, a mercapto group or a naphthyl group. Examples of the base include KOH, $KOCH_3$, $KOCH(CH_3)_2$, $KC_{10}H_8$, NaOH, $NaOCH_3$, LiOH, $LiOCH_3$, and LiOCH$(CH_3)_2$. Quaternary ammonium salts are also useful as a base.

The base is used usually at a molar ratio of 1/10 to 1/1,000, preferably 1/20 to 1/100, to the 2-substituted cyclohexanone substrate.

The nitrogen compound used in the catalyst system of the invention is such a nitrogen-containing compound as an amine compound and an optically active amine compound.

The amine compound or optically active amine compound includes a monoamine represented by formula (V):

$$NR^5R^6R^7 \qquad (V)$$

wherein $R^5$, $R^6$, and $R^7$ each represent a hydrogen atom, an alkyl group or an aryl group;

an optically active monoamine represented by formula (V) in which at least one of $R^5$, $R^6$, and $R^7$ is an optically active group, and an optically active diamine compound represented by formula (VI):

wherein $R^8$, $R^9$, $R^{14}$, $R^{15}$ each represent a hydrogen atom, an alkyl group, an aryl group, a urethane group, a sulfonyl group, etc.; $R^{10}$, $R^{11}$, $R^{12}$, and $R^{13}$ each represent a hydrogen atom, an alkyl group, an aryl group, a cycloalkyl group, etc.; in the optically active diamine compound $R^{10}$, $R^{11}$, $R^{12}$, and $R^{13}$, which may be the same or different, are selected from a hydrogen atom, an alkyl group, an aryl group, a cyclic hydrocarbon group, etc. so that the carbon atoms to which they are bonded may become asymmetric centers.

Examples of the amine compounds are n-propylamine, isopropylamine, n-butylamine, isobutylamine, sec-butylamine, tert-butylamine, benzylamine, dibenzylamine, triethylamine, aniline, 1,2-phenylenediamine, ethylenediamine, 1,2-propanediamine, 1,3-propanediamine, 1,2-butanediamine, 1,3-butanediamine, 1,4-butanediamine, 2,3-butanediamine, 1,2-pentanediamine, 1,3-pentanediamine, 1,4-pentanediamine, 1,5-pentanediamine, 2,3-pentanediamine, 2,4-pentanediamine, 2-methyl-1,2-propanediamine, 3-methyl-1,3-butanediamine, 4-methyl-2,3-pentanediamine, and 2-methyl-2,4-pentanediamine.

Examples of the optically active amine compounds are phenylethylamine, α-naphthylethylamine, 2-butylamine, 1,2-diphenylethylenediamine, 1,2-cyclohexanediamine, 1,2-cycloheptanediamine, 2,3-dimethyl-2,3-butanediamine, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphthylethylenediamine, 1-isobutyl-2,2-dinaphthylethylenediamine, and 1-isopropyl-2,2-dinaphthylethylenediamine; and optically active diamine compounds of formula (VI) in which one or both of $R^8$ and $R^{14}$ is/are a sulfonyl group or a urethane group.

The optically active amine compounds useful in the invention are not limited to the foregoing examples. Optically active propanediamine, butanediamine, and phenylenediamine derivatives are also useful. The monoamine compound or optically active monoamine compound is used in an amount of 1 to 4 equivalents, preferably 2 to 4 equivalents, to the transition metal complex, and the diamine compound or optically active diamine compound is used in an amount of 0.5 to 2.5 equivalents, preferably 1 to 2 equivalents, to the transition metal complex.

The solvent to be used in the reaction is selected appropriately from those solubilizing the reaction substrate and the catalyst system. Suitable solvents include alcohols, such as methanol, ethanol, 2-propanol, butanol, and benzyl alcohol; ethers, such as ethyl ether, tetrahydrofuran, and dioxane; esters, such as ethyl acetate, isopropyl acetate, and butyl acetate; halogen-containing hydrocarbons, such as methylene chloride; and hetero atom-containing organic solvents, such as N,N'-dimethylformamide and dimethyl sulfoxide. Alcohol solvents are preferred, with 2-propanol being still preferred. A mixture of two or more of the above-described solvents may be used for sparingly soluble substrates.

The amount of the solvent to be used is decided according to the solubility of the reaction substrate and economy. In using 2-propanol, for example, the reaction can be carried out at a substrate concentration broadly ranging from 1% or even lower up to a nearly solvent-free condition. A preferred substrate concentration is 5 to 50% by weight.

The asymmetric hydrogenation reaction can proceed under atmospheric pressure because of the high activity of the catalyst system. From the economical consideration a suitable hydrogen pressure is from 1 to 100 atm., particularly 5 to 50 atm.

The reaction temperature is from −20° to 100° C., preferably −5° to 50° C., still preferably 0° to 30° C. The reaction time varies depending on the reaction conditions, such as substrate concentration, temperature, and hydrogen pressure. The reaction usually completes in several minutes to 24 hours.

The reaction can be conducted either in a batch system or in a continuous system.

The present invention will now be illustrated in greater detail with reference to Examples, but it should be understood that the invention is not limited thereto. The products prepared were identified from the infrared absorption spectrum (IR) (Model IR-810, manufactured by Nippon Bunko Kogyo K.K.) and the $^1$H nuclear magnetic resonance spectrum ($^1$H-NMR) (Model AM-400, manufactured by Bruker Inc.; internal standard: tetramethylsilane in $CDCl_3$).

The conversions, diastereoselectivity, and enantioselectivity of the products obtained were confirmed by gas chromatography under the following conditions.

Conversion

Gas Chromatograph: HP-5890 series II Plus, manufactured by Hewlett Packard
  Column: Neutrabond-1 (0.25 mm×30 m), manufactured by G. L. Science Co., Ltd.
  Carrier gas: helium
  Injection temperature: 220° C.
  Detector temperature: 250° C.
  Initial temperature: 80° C.
  Final temperature: 250° C.
  Rate: 2° C./min Diastereoselectivity Gas chromatograph: HP-5890, manufactured by Hewlett Packard
  Column: DB-WAX (0.53 mm×15 m), manufactured by JIW Scientific Co.
  Carrier gas: helium
  Injection temperature: 200° C.
  Detector temperature: 250° C.
  Initial temperature: 60° C.
  Final temperature: 200° C.
  Rate: 2° C./min Enantioselectivity Gas chromatograph: GC-14A, manufactured by Shimadzu Corp.
  Column: Chirasil-DEX CB (0.25 mm×25 m), manufactured by Chrompack International b.v.
  Carrier gas: helium
  Injection temperature: 220° C.
  Detector temperature: 250° C.
  Initial temperature: 50° C.
  Final temperature: 150° C.
  Rate: 1° C./min

EXAMPLE 1

In a 100 ml autoclave were charged 3.4 ml of a 0.1M solution of potassium hydroxide (0.34 mmol) in 2-propanol, 4.2 mg (0.02 mmol) of (1R,2R)-diphenylethylenediamine, 1.28 g (10.0 mmol) of 2-methoxycyclohexanone, 9.5 mg (0.005 mmol) of $Ru_2Cl_4[(R)\text{-DM-BINAP}]_2NEt_3$, and 6.5 ml of 2-propanol in a nitrogen atmosphere, and hydrogen was introduced therein to 50 atm. The mixture was stirred at 50° C. for 30 minutes and cooled to room temperature. The disappearance of the starting material was confirmed by gas chromatography. The solvent was evaporated under reduced pressure, and the residue was distilled under reduced pressure to obtain (1S,2R)-2-methoxycyclohexanol. The optical purity of the product was found to be 98% d.e. and 96% e.e. by gas chromatography.

Boiling Point: 80°–82° C./24 mmHg

IR (neat) $cm^{-1}$: 3450, 1100

NMR ($CDCl_3$): 1.2–1.4 (m, 2H), 1.45–1.7 (m, 2H), 1.7–1.9 (m, 2H), 2.22 (dd, J=1.0, 5.0 Hz, 1H), 3.28 (ddd, J=3.1, 3.3, 10.0 Hz, 1H), 3.37 (s, 3H), 3.8–3.9 (m, 1H)

EXAMPLE 2

In a 100 ml autoclave were charged 3.4 ml of a 0.1M solution of potassium hydroxide (0.34 mmol) in 2-propanol, 4.2 mg (0.02 mmol) of (1S,2S)-diphenylethylenediamine, 1.28 g (10.0 mmol) of 2-methoxycyclohexanone, 8.4 mg (0.005 mmol) of $Ru_2Cl_4[(S)\text{-BINAP}]_2NEt_3$, and 6.5 ml of 2-propanol in a nitrogen atmosphere, and hydrogen was introduced therein to 50 atm. The mixture was stirred at 50° C. for 60 minutes and cooled to room temperature. The disappearance of the starting material was confirmed by gas chromatography. The solvent was evaporated under reduced pressure, and the residue was distilled under reduced pressure to obtain (1R,2S)-2-methoxycyclohexanol. The optical purity of the product was found to be 97% d.e. and 92% e.e. by gas chromatography.

EXAMPLE 3

In a 100 ml autoclave were charged 1.75 ml of a 0.2M solution of potassium hydroxide (0.35 mmol) in 2-propanol, 0.2 ml of a 0.1M solution of 1,3-propanediamine (0.02 mmol) in 2-propanol, 1.28 g (10.0 mmol) of 2-methoxycyclohexanone, 8.4 mg (0.005 mmol) of $Ru_2Cl_4[(S)\text{-BINAP}]_2NEt_3$, and 8 ml of 2-propanol in a nitrogen atmosphere, and hydrogen was introduced therein to 50 atm. The mixture was stirred at room temperature for 1.5 hours. The disappearance of the starting material was confirmed by gas chromatography. The solvent was evaporated under reduced pressure, and the residue was distilled under reduced pressure to obtain (1R,2S)-2-methoxycyclohexanol. The optical purity of the product was found to be 93% d.e. and 91% e.e. by gas chromatography.

EXAMPLE 4

In a 100 ml autoclave were charged 1.5 ml of a 0.2M solution of potassium hydroxide (0.30 mmol) in 2-propanol, 1.1 mg of (0.005 mmol) of (1S,2S)-diphenylethylenediamine, 1.28 g (10.0 mmol) of 2-methoxycyclohexanone, 1.9 mg (0.0001 mmol) of $Ru_2Cl_4$[(S)-DM-BINAP]$_2$NEt$_3$, and 8.5 ml of 2-propanol in a nitrogen atmosphere, and hydrogen was introduced therein to 50 atm. The mixture was stirred at room temperature for 3.5 hours; The disappearance of the starting material was confirmed by gas chromatography. The solvent was evaporated under reduced pressure, and the residue was distilled under reduced pressure to obtain (1R,2S)-2-methoxycyclohexanol. The optical purity of the product was found to be 99% d.e. and 98% e.e. by gas chromatography.

EXAMPLE 5

In a 100 ml autoclave were charged 1.50 ml of a 0.2M solution of potassium hydroxide (0.30 mmol) in 2-propanol, 4.2 mg (0.02 mmol) of (1R,2R)-diphenylethylenediamine, 1.28 g (10.0 mmol) of 2-methoxycyclohexanone, 9.6 mg (0.01 mmol) of Rh(COD)[(R)-T-BINAP]BF$_4$, and 8.5 ml of 2-propanol in a nitrogen atmosphere, and hydrogen was introduced therein to 50 atm. The mixture was stirred at 50° C. for 19 hours and cooled to room temperature. The disappearance of the starting material was confirmed by gas chromatography. The solvent was evaporated under reduced pressure, and the residue was distilled under reduced pressure to obtain (1S,2R)-2-methoxycyclohexanol. The optical purity of the product was found to be 34% d.e. and 14% e.e. by gas chromatography.

EXAMPLE 6

In a 100 ml autoclave were charged 1.5 ml of a 0.2M solution of potassium hydroxide (0.30 mmol) in 2-propanol, 4.2 mg (0.02 mmol) of (1S,2S)-diphenylethylenediamine, 1.28 g (10.0 mmol) of 2-methoxycyclohexanone, 10.1 mg (0.01 mmol) of Ir(COD)[(S)-BINAP]BF$_4$, and 8.5 ml of 2-propanol in a nitrogen atmosphere, and hydrogen was introduced therein to 50 atm. The mixture was stirred at 50° C. for 19 hours and cooled to room temperature. The disappearance of the starting material was confirmed by gas chromatography. The solvent was evaporated under reduced pressure, and the residue was distilled under reduced pressure to obtain (1R,2S)-2-methoxycyclohexanol. The optical purity of the product was found to be 78% d.e. and 31% e.e. by gas chromatography.

EXAMPLES 7 TO 26

In the same manner as in Examples 1 to 6 the 2-substituted cyclohexanone shown below was asymmetrically hydrogenated in the presence of a catalyst system using the phosphine ligand shown below and the amine shown below under the reaction conditions shown in Table 1 to obtain the corresponding optically active cyclohexanol in high yield. The reaction results are shown in Table 1.

2-Substituted Cyclohexanone:

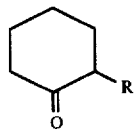

19: R = OCH$_3$
20: R = OC$_2$H$_5$
21: R = CH$_3$

Phosphine Ligand:

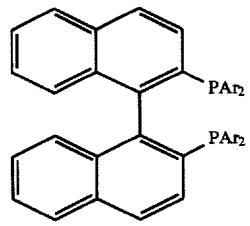

1: Ar = C$_6$H$_5$(BINAP)
2: Ar = C$_6$H$_4$-p-Me(Tol-BINAP)
3: Ar = C$_6$H$_3$-3,5-Me$_2$(DM-BINAP)
4: Ar = C$_6$H$_4$-p-MeO(p-MeO-BINAP)
5: Ar = C$_6$H$_4$-p-Cl(p-Cl-BINAP)
6: Ar = C$_6$H$_4$-p-$^t$Bu(p-$^t$Bu-BINAP)

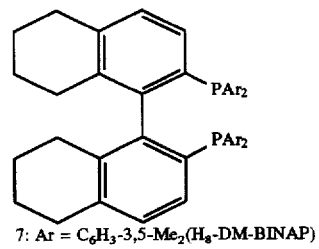

7: Ar = C$_6$H$_3$-3,5-Me$_2$(H$_8$-DM-BINAP)

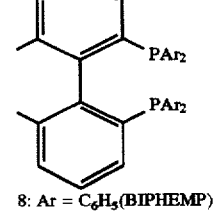

8: Ar = C$_6$H$_5$(BIPHEMP)

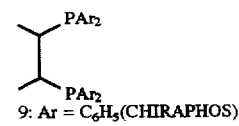
9: Ar = C$_6$H$_5$(CHIRAPHOS)

Amine:

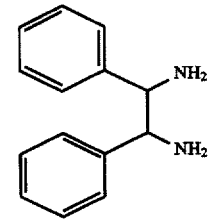

(S,S)-10
(R,R)-10

-continued

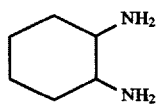

(S,S)-11

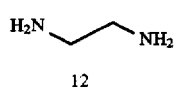

12

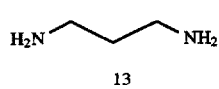

13

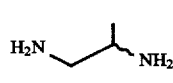

14

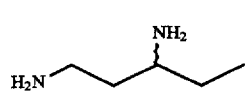

15

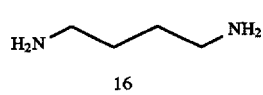

16

17 tert-BuNH$_2$

18

As described and demonstrated above, the present invention makes it possible to obtain various optically active cyclohexanol derivatives at high purity and in high yield.

While the invention has been described in detail and with reference to specific examples thereof, it will be apparent to one skilled in the art that various changes and modifications can be made therein without departing from the spirit and scope thereof.

What is claimed is:

1. A process for producing an optically active cyclohexanol derivative represented by formula (I):

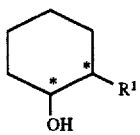

(I)

wherein R$^1$ represents an alkyl group having 1 to 4 carbon atoms, a hydroxyl group, or a protected hydroxyl group, comprising asymmetrically hydrogenating a cyclohexanone derivative represented by formula (II):

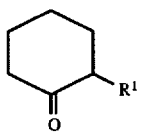

(II)

wherein R$^1$ is as defined above, in the presence of a catalyst system for asymmetric hydrogenation composed of a transition metal compound, a base, and a nitrogen compound, wherein the base is a compound represented by formula (IV):

$$M^2Y \qquad (IV)$$

wherein M$^2$ represents an alkali metal or an alkaline earth metal; and Y represents a group selected from a hydroxyl

TABLE 1

| | Catalyst Component | | | Reaction Conditions | | | Reaction Results | | | |
|---|---|---|---|---|---|---|---|---|---|---|
| | | | | Hydrogen | | | | | | |
| Example No. | Carbonyl Compound | Phosphine Ligand | Amine | Pressure (atm) | Temp. (°C.) | Time (hr) | Yield (%) | % d.e. | % e.e. | Config-uration |
| 7 | 19 | (S)-1 | (S, S)-10 | 50 | r.t. | 14 | >99 | 98 | 95 | (1R, 2S) |
| 8 | 19 | (S)-2 | (S, S)-10 | 50 | 50 | 2.5 | >99 | 96 | 89 | (1R, 2S) |
| 9 | 19 | (R)-4 | (R, R)-10 | 50 | 50 | 1.5 | >99 | 93 | 81 | (1S, 2R) |
| 10 | 19 | (R)-5 | (R, R)-10 | 50 | 50 | 3 | >99 | 92 | 82 | (1S, 2R) |
| 11 | 19 | (S)-6 | (S, S)-10 | 50 | r.t. | 40 | 98 | 97 | 93 | (1R, 2S) |
| 12 | 19 | (R)-7 | (R, R)-10 | 50 | 50 | 0.5 | >99 | 98 | 91 | (1S, 2R) |
| 13 | 19 | (S)-7 | (S, S)-10 | 50 | 50 | 1 | >99 | 96 | 89 | (1R, 2S) |
| 14 | 20 | (S)-1 | (S, S)-10 | 50 | r.t. | 20.5 | >99 | 97 | 92 | (1R, 2S) |
| 15 | 19 | (S)-1 | 12 | 50 | r.t. | 1.5 | >99 | 96 | 87 | (1R, 2S) |
| 16 | 19 | (S)-1 | 13 | 10 | r.t. | 1.5 | >99 | 93 | 91 | (1R, 2S) |
| 17 | 19 | (S)-1 | 14 | 50 | r.t. | 1.5 | >99 | 96 | 86 | (1R, 2S) |
| 18 | 19 | (S)-1 | 15 | 50 | r.t. | 2 | >99 | 93 | 90 | (1R, 2S) |
| 19 | 21 | (S)-1 | (R, R)-10 | 50 | r.t. | 4.5 | >99 | 94 | 75 | (1S, 2R) |
| 20 | 19 | (R)-8 | (R, R)-10 | 50 | 50 | 2 | >99 | 96 | 91 | (1S, 2R) |
| 21 | 19 | (S, S)-9 | (S, S)-10 | 50 | 50 | 4 | 95 | 40 | 45 | (1R, 2S) |
| 22 | 19 | (S)-1 | (S, S)-11 | 50 | 50 | 17 | >99 | 90 | 75 | (1R, 2S) |
| 23 | 19 | (S)-1 | 16 | 50 | r.t. | 69 | 99 | 88 | 66 | (1R, 2S) |
| 24 | 19 | (S)-1 | 17 | 50 | r.t. | 4.5 | 91 | 94 | 84 | (1R, 2S) |
| 25 | 19 | (S)-1 | 18 | 50 | r.t. | 22 | >99 | 86 | 70 | (1R, 2S) |
| 26 | 19 | (S)-1 | (R, R)-10 | 50 | r.t. | 23 | >99 | 95 | 90 | (1R, 2S) | group, an alkoxy group, a mercapto group, a naphthyl croup, or a quaternary ammonium salt and wherein the nitrogen compound is an amine compound.

2. The process according to claim 1, wherein said the transition metal compound is a complex of a transition metal of the group VIII represented by formula (III):

$$M^1X_mL_n \quad (III)$$

wherein $M^1$ represents a transition metal selected from Ru, Rh, Ir, and Pt; X represents a hydrogen atom, a halogen atom, a carboxyl group, a hydroxyl group, and an alkoxy group; L represents an optically active phosphine ligand; and m and n each represent an integer.

3. The process according to claim 1, wherein said asymmetric hydrogenation is carried out in an organic solvent.

4. The process according to claim 2, wherein the transition metal compound is used in a molar ratio of 1/100 to 1/100,000 to the cyclohexanone derivative represented by formula (II).

5. The process according to claim 4, wherein the amine compound or optically active amine compound is a monoamine represented by formula (V):

$$NR^5R^6R^7 \quad (V)$$

wherein $R^5$, $R^6$, and $R^7$ each represent a hydrogen atom, an alkyl group or an aryl group; or an optically active monoamine represented by formula (V) in which at least one of $R^5$, $R^6$, and $R^7$ is an optically active group, or an optically active diamine compound represented by formula (VI):

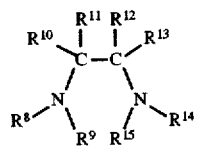

wherein $R^8$, $R^9$, $R^{14}$, and $R^{15}$ each represent a hydrogen atom, an alkyl group, an aryl group, a urethane group or a sulfonyl group; $R^{10}$, $R^{11}$, $R^{12}$, and $R^{13}$ each represent a hydrogen atom, an alkyl group, an aryl group or a cycloalkyl group; and in the optically active diamine compound $R^{10}$, $R^{11}$, $R^{12}$, and $R^{13}$, which are the same or different, are selected from a hydrogen atom, an alkyl group, an aryl group or a cyclic hydrocarbon group so that the carbon atoms to which $R^{10}$, $R^{11}$, $R^{12}$, and $R^{13}$ are bonded become asymmetric centers, and wherein the monoamine compound or optionally active monoamine is used in an amount of 1 to 4 equivalents to the transition metal complex and the optically active diamine compound is used in an amount of 0.5 to 2.5 equivalents to the transition metal complex.

6. The process according to claim 5, wherein the base is used in a molar ratio of 1/10 to 1/1,000 to the cyclohexanone derivative represented by formula (II).

7. The process according to claim 6, wherein the process is conducted at a hydrogen pressure of from 1 to 100 atm., at a temperature of from −20° to 100° C. and for a time of from several minutes to 24 hours.

* * * * *